United States Patent [19]

Adams

[11] Patent Number: 4,826,477
[45] Date of Patent: May 2, 1989

[54] CONNECTOR FOR BLOOD HANDLING SYSTEMS

[75] Inventor: Bruce B. Adams, Malden, Mass.

[73] Assignee: ABIOMED Cardiovascular, Inc., Danvers, Mass.

[21] Appl. No.: 93,592

[22] Filed: Sep. 10, 1987

Related U.S. Application Data

[63] Continuation-in-part of Ser. No. 909,828, Sep. 19, 1986, abandoned.

[51] Int. Cl.$^4$ ............................................. A61M 37/00
[52] U.S. Cl. ..................................... 604/4; 604/283; 128/334 C
[58] Field of Search ........................................ 604/4-6, 604/175, 283, 905, 408-410; 128/334 C

[56] References Cited

U.S. PATENT DOCUMENTS 4,049,034 9/1977 Vcelko et al. ....................... 604/408
4,588,402 5/1986 Igari et al. .

Primary Examiner—John D. Yasko
Assistant Examiner—Mark F. Colosimo
Attorney, Agent, or Firm—Nutter, McClennen & Fish

[57] ABSTRACT

A connector for connecting a flexible conduit which is used to contain blood flow in a extra-corporeal blood handling system to a second component in said system. The connector includes a dual-acting coupler with a first coupling section for joining to the flexible conduit and a second coupling section, which can be of conventional design, for joining to the second component. The first coupling section includes an outer tapered portion which tapers inward to a rounded thin edge at the end of the coupler. The connector further includes a generally ring-shaped compression collar having an inner tapered portion for encircling the outer tapered portion of the coupler, with the angle of taper of the inner tapered portion of the collar being at least as large as the angle of taper of the outer tapered portion of the coupler. When the collar is assembled over the tapered portion of the coupler with the flexible conduit therebetween, the two facing tapered portions compress the flexible conduit and focus the compression in the vicinity of the rounded edge of the coupler. This forms a tight seal at the juncture of the conduit and the coupler, thereby minimizing any gaps in the wall at the juncture which can cause blood coagulation by flow stagnation.

6 Claims, 3 Drawing Sheets

CONNECTOR FOR BLOOD HANDLING SYSTEMS

RELATED APPLICATIONS

This application is a continuation-in-part of U.S. patent application Ser. No. 909,828, filed Sept. 19, 1986 now abandoned.

BACKGROUND OF THE INVENTION

1. Field of the Invention

This invention generally relates to extra-corporeal, blood handling machines which are connected to the blood stream to process blood outside the body and, more specifically, it relates to the interconnections between flexible components which are used to contain blood flow such as blood tubing and the connectors which are used in blood handling machines such as ventricular assist, artificial kidney and heart-lung machines.

2. Description of the Prior Art

A serious problem plagues extra-corporeal, blood handling machines. While circulating blood, the machines tend to generate dangerous blood cell aggregates such as clots in areas of blood stasis and thrombi in areas of flow disturbances. (For the purposes of this application, the terms clot and thrombus will be used interchangeably.) The problem is serious because the presence of small blood clots within the human cardiovascular system can seriously impair the patient, resulting in strokes, organ impairment and even death.

The medical community is aware that the connectors that connect blood tubing to other components in the blood circuits involving these machines have been a primary site of blood clot generation. In an effort to solve the clotting problem which exists at those junctions, two different but related avenues of research have been pursued. Both avenues concern the blood compatibility of blood contacting surfaces. However, neither avenue has produced satisfactory results. Therefore, an acceptable solution to the blood clotting problem at the junctions has remained elusive.

One avenue of research has involved efforts to create an environment in the blood tubing connectors which simulates the environment found in the living body. The blood vessels of the body are coated with an intima consisting of an endothelial lining backed by connective tissue. Since blood clotting is not a problem along the intact intima, a segment of the medical community has believed that it can solve the clotting problem by encouraging pseudo intimas to grow on the inner surfaces of the connectors. This approach has had limited success but it also has presented other unacceptable problems. Once a pseudo intima is established, it may fail by delaminating from the substrate. If the pseudo intima does not delaminate, it continues to grow thicker with time. However, since the pseudo intima does not have its own blood vessels, the base layers eventually die and slough off into the blood flow. In either case, the deterioration of the pseudo intima presents a problem as serious as the blood clots.

Another avenue of research has focused on an effort to find better blood-compatible materials out of which connectors and tubing can be constructed. An underlying rationale for this approach is that the chemical composition of the connector materials elicits the clotting problem. In this search, thousands of materials have been examined for better blood-compatibility. As of yet, however, better materials have not been found which alone solve the clotting problem.

Since no satisfactory way has been found to eliminate the sources of blood clots around the tubing-connectors, two methods have been used to remove the clots before they cause serious damage. One method filters the clots out of the blood after it passes through the machine; the other method dissolves the clots by administering anticoagulants. Both methods are unsatisfactory solutions to the problem. Removal of blood clots through filtering tends to activate clotting mechanisms within the filter itself and generate other clots which threaten harm to the patient. The alternative of dissolving clots with anticoagulants forces the doctor to delicately balance two life-threatening phenomena. Administering too much anticoagulant can cause spontaneous internal bleeding, especially in the patients that may be platelet depleted; whereas administering too little will not effectively eliminate the clots. It is difficult to arrive at a dosage that avoids both problems.

SUMMARY OF THE INVENTION

The principal object of this invention is to reduce blood clot/thrombus formation in the vicinity of the junctions between flexible components such as blood tubing and the connectors used in extra-corporeal, blood handling systems.

It has been found that the clotting problem associated with the tubing-connector junctions, stems from the fluid mechanics of the blood flow at these junctions and that the solution to this problem is to structurally modify these junctions as described herein. It has been known that blood which is permitted to come to a quasi-stagnant state on the surface of a foreign material tends to form clots which attach to that surface and then grow by accretion. Normally, the blood inside blood handling systems flows continually, so blood stagnation would not appear to be a problem. Nevertheless, tubing-connector junctions, which had been in service on such machines, were closely examined upon retrieval to determine if the blood-stagnation mechanism might be causing the clotting.

These examinations reveal that clots have been forming at locations where discontinuities exist on the inner walls of the junctions. In particular, the discontinuities are located around the ends of the connectors at the junctures where they meet the inside walls of the tubing. These discontinuities result in annular pockets at these junctures. Typically, they are caused by an excessively wide edge on the connectors or by pockets or gaps which are caused by separations between the tubing and the connector. The separations appear to result from bending strains on the tubing which distort it from its normally circular cross section at its juncture with the connector. In any case, I have discovered that the discontinuities have sufficiently disrupted the blood flow at the surface to permit blood to come to a quasi-stagnant state long enough to form clots which then grew and could detach into the blood stream.

More specifically, on smooth surfaces within blood handling machines, a mechanism for preventing clot formation is present during normal system operation. The blood flow rate along the smooth surfaces of the tubing walls reduces the possibility of clot formation by (a) limiting the time that blood clotting constituents can spend near the surface in order to generate a clot and (b) exerting a shear force which prevents blood corpuscles from sticking at any one place on the wall long enough to form clots. As long as the shear force is above a critical level, clot generation is not a problem on the tubing walls. However, at discontinuities in the wall, such as at the tubing-connector junctions, residence times of the blood constituents increases and the shear forces are reduced compared to those associated with normal blood flow rate along a smooth wall. Thus, blood corpuscles which are caught in those regions are more likely to come to rest in quasi-stagnant locations at the discontinuities and reside there for longer times than they would on a smooth wall. If a discontinuity is large enough, the residence times become longer than a critical level and a clot forms and grows by accretion at that point. Thus the large discontinuities cause serious clot generation problems.

The invention reduces the magnitudes of the discontinuities at junctions between blood tubing and connectors. The invention accomplishes this result by means of an improved connector, specifically the portion of the connector that couples to the tubing. The connector has a collar and a conventional tubing coupler which has a coupling section for coupling to another connector and a tubing section that joins the connector to the tubing. The tubing section of the tubing coupler has barbs. The tubing section has the same inside diameter as the tubing, and, in addition to circular ridges that form the barbs on it, this end has a tapered portion that terminates in a thin edge. The tubing is fitted tightly over this end where it conforms to the taper and is held securely in place by the ridges. In the assembled connection, the thin edge lies inside the tubing and defines the juncture of the inner surfaces of the tubing coupler and the tubing. The collar has a tapered section with a tapered inner surface which matches to the tubing coupler. The matching inner surface of the collar compresses the tubing against the tubing coupler and forms a seal at the juncture near the thin edge. Preferably, the collar also has a tubular neck section that extends away from the tubing coupler and which snugly encircles the tubing. The neck section prevents the tubing from flexing in the vicinity of the tubing-connector juncture and tends to hold the collar in place.

The invention minimizes the discontinuities at the juncture in the following ways. First, the thin edge at the outer end of the tubing section is made smaller than the largest permissible depth of the discontinuity. Secondly, the seal formed by the compression of the tubing between the tapered portion of the tubing coupler and the matching inner surface of the collar closes any pre-existing gaps between the tubing and the tubing section which might result from misalignment. The compression also tends to shrink the annular pocket at the juncture. Finally, the neck section prevents bending strains on the tubing from reaching the thin edge and creating new discontinuities by deforming the tubing away from the tubing coupler at that location.

The performance of a system using the connectors embodying the invention is markedly superior to the performance of the same system using prior connectors. Empirical evidence confirms that the invention essentially eliminates blood clot generation at these points. Typically, clots leave clearly visible tracks or imprints at the locations where they form and from which they detach to disperse into the cardiovascular system. Upon disassembly of prior tubing-connector junctions after months of operation, such tracks or imprints provide abundant evidence of the blood clot formation which has occurred. In contrast, with connectors embodying the invention, the unctions are devoid of blood clots and blood clot indicating tracks, even after months of operation.

BRIEF DESCRIPTION OF THE DRAWINGS

This invention is pointed out with particularity in the appended claims. The above and further objects and advantages of this invention may be better understood by referring to the following detailed description, taken in conjunction with the accompanying drawings, in which:

DESCRIPTION OF THE PREFERRED EMBODIMENTS

Figure 1:
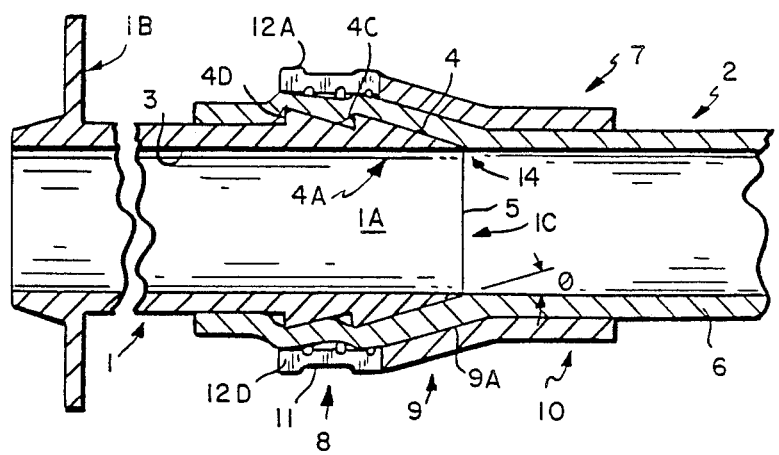
FIG. 1 is a detailed cross-sectional view of the completely assembled connector embodying the invention with the cross-section being taken along the axis of the connector.
Figure 1A:
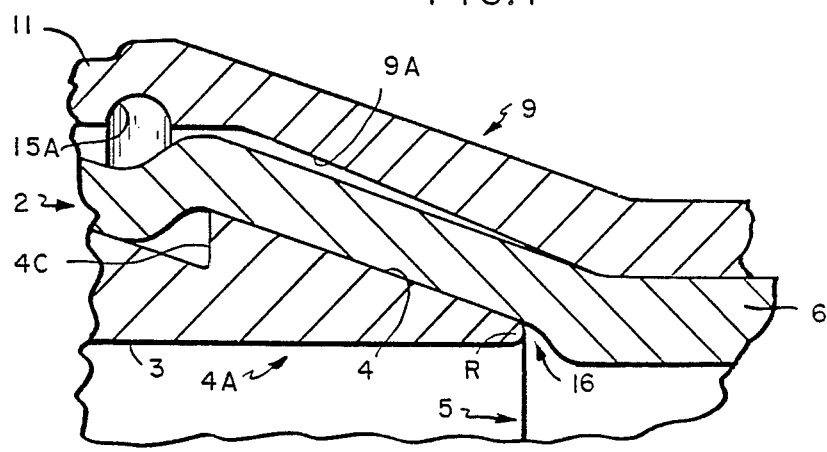
FIG. 1A is an enlarged view of the tubing-connector juncture.

FIG. 1 illustrates in a cross-sectional view a blood tubing connection which embodies the invention. The connection, which is used in an extra-corporeal, blood-handling system comprises a tubing coupler 1, a flexible tubing 2 and a collar 7. The tubing coupler 1 is generally tubular in shape. It has a tubing section 1A with an outer end 1C with a uniform inside diameter D1 and it has a coupling section 1B. The tubing coupler 1 has a continuous inside surface 3 with a uniform inside diameter D1. The coupling section 1B mates with another connector (not shown); thus its design depends upon the structure of the connector with which it mates. The tubing section 1A has an outer surface 4 over which the tubing 2 fits. The outer surface 4 consists of a tapered portion 4A and ridges 4C and 4D that are contoured to form annular barbs. The tapered portion 4A meets the inside surface 3 at a taper angle $\phi$ to form a thin edge 5 at the outer end 1C of the tubing section 1A. The thickness of the edge 5 is defined by a radius of curvature R (FIG. 1A). The tubing coupler is made from a material, such as polycarbonate, which is blood compatible and is also rigid so that the tubing coupler is not easily deformed during normal usage.

The flexible tubing 2 has a uniform outside diameter D2, a uniform inside diameter D3 which is equal to the inside diameter D1 of the tubing section 1A, and a wall 6. The tubing 2 is typically made from a transparent polyvinyl chloride material which is flexible and which is sufficiently elastic to permit the tubing 2 to stretch slightly so that it can be forced over the outer surface 4 of the tubing coupler 1. When the tubing 2 is fitted over the tubing section 1A, a juncture 14 is formed in the vicinity of edge 5 where the tubing 2 and the tubing section 1A meet.

Figure 2:
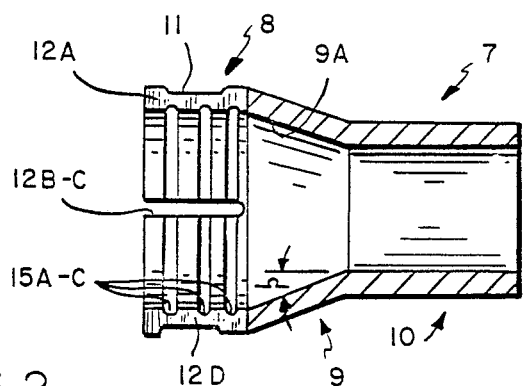
FIG. 2 is a cross-sectional view of the collar which is part of the connector with the cross-section being taken along the axis of the collar.

The collar 7, which is more clearly illustrated in the cross-sectional view of FIG. 2, is of unitary construction and has at least two sections: a taper section 9 and a tubular neck section 10 extending from the narrow end thereof. The section 9 has a length approximately equal to the length of the tapered portion 4A of the tubing coupler 1 and has an inside surface 9A which has a taper angle $\Omega$. The angle $\Omega$ is preferably from zero degrees to 5 degrees greater than the angle $\phi$.

The neck section 10 has an inside diameter D4. The diameter D4 is slightly smaller than the outside diameter D2 of the tubing 2 but still large enough to permit the tubing 2 to pass through it. For example, D4 can be selected to be approximately equal to 0.95 times the diameter D2.

The components are assembled by first sliding the collar 7, neck section 10 first, over the tubing 2. Then the tubing 2 is forced onto the tubing section 1A of the tubing coupler 1 so that it conforms to the outer surface 4 of the tubing section 1A, as illustrated in FIG. 1. In this mounted configuration, the tubing 2 flares out over the tapered portion 4A and the ridges 4C and 4D tend to hold the tubing in place so that it does not slide off the tubing coupler 1. Next the collar 7 is pushed into an engaged position over the connection formed by the tubing 2 and the tubing coupler 1 so that the inner surface 9A compresses the tubing 2 against the tapered portion 4A of the tubing coupler 1. Since the inside diameter D4 of the neck section 10 is slightly smaller than the outside diameter D2 of the tubing 2, the neck section 10 compresses the tubing 2 which passes through the neck section 10.

The compression of the tubing 2 between the inside surface 9A and the tapered portion 4A forms a seal at the juncture 14 of the tubing 2 and the tubing coupler 1. Since the angle $\Omega$ is equal to or slightly larger than the angle of taper $\phi$ and D2 is slightly smaller than D4, the compression of the tubing is greatest near the edge 5 of the tubing coupler 1. This causes the seal to focus around the edge 5. The compression thus urges the tubing 2 to conform with the surface of th tubing section 1A at and in the vicinity of edge 5, i.e. at the juncture 14 of the tubing 2 and the tubing coupler 1. Further, it prevents the tubing 2 from separating from the tubing coupler 1 at the edge 5, thereby essentially eliminating any gaps, which might be caused by the tubing 2 not properly conforming to the tapered portion 4a, e.g. because of misalignment when the tubing and tubing coupler are joined together.

The presence of some discontinuity in the tubing-connector junction is unavoidable. In particular, a discontinuity, in the form of an annular pocket 16 (FIG. 1A), will exist at edge 5 where the inside surface 3 of the tubing coupler 1 meets the tubing 2. For example, because of material and fabrication limitations, there is a practical lower limit on the radius R. Experience has shown that, for tubing couplers made of polycarbonate, an edge with a radius R of at least about 0.005 inches will possess a desirable durability. This, together with the fact that the tubing 2 cannot have an absolutely sharp bend where it meets the taper portion 4A, makes a small discontinuity unavoidable. However, experimental studies have indicated that if the discontinuity is smaller in the radial direction than about 0.015 inches, blood clotting problems will not occur at that location under the blood flow rates experienced in extra-corporeal blood handling machines. Therefore, if the edge 5 is thin, i.e. if the radius R lies in a range of about 0.005 to 0.010 inches, the discontinuity caused by the edge 5 will not generate clots.

Also, for practical reasons, the angle $\phi$ should lie in the range from about 15 degrees to 25 degrees. If the angle $\phi$ is made much smaller than 15 degrees, the tapered portion 4A will be impractically long and the tubing coupler will become too thin and weak near the edge 5 of the tubing section 1A. On the other hand, if the angle $\phi$ is made much larger than 25 degrees, forcing the tubing 2 onto the tubing coupler 1 will become difficult and the large angle will tend to deform the tubing 2 so that it does not naturally conform to the tapered portion 4A in the vicinity of edge 5.

The neck section 10 on the collar 7 serves a dual purpose. Since the neck section 10 compresses the tubing 2, it tends to reduce the size of the annular pocket 16 and thus the size of discontinuity in the juncture region 14 which disrupts the blood flow in that region. In addition, the neck section 10 isolates the juncture region 14 from strains caused by inadvertent or unavoidable flexing of the tubing 2. If the tubing 2 is permitted to flex in the vicinity of the juncture region 14, the tubing 1 may be pulled away from the tubing coupler 1 thus creating new discontinuities or gaps in the vicinity of the edge 5 which act as blood clot generation sites. The neck section 10 assures that this does not occur.

An optional feature is a gripping section 8 at the large end of the taper section 9 of the collar 7. This provides a means for holding the collar 7 in place when it is properly engaged. The gripping section 8 may take a number of different forms, one of which is shown in FIG. 2. As illustrated, it includes an annular recess 11. In addition, at equally spaced locations around the circumference of the section 8, there are slots 12A-D which extend the length of the gripping section 8. Circling the inside surface of the gripping section are grooves 15A-C. By binding the gripping section 8 with a tie rap (not shown) disposed within the annular recess 11, it may be compressed to grasp the tubing 2 and firmly anchor the collar 7 in place in the engaged position. The grooves 15A-C provide an articulated surface which further assists in anchoring the collar 7 so that it will not slide away from the engaged position.

Figure 3:
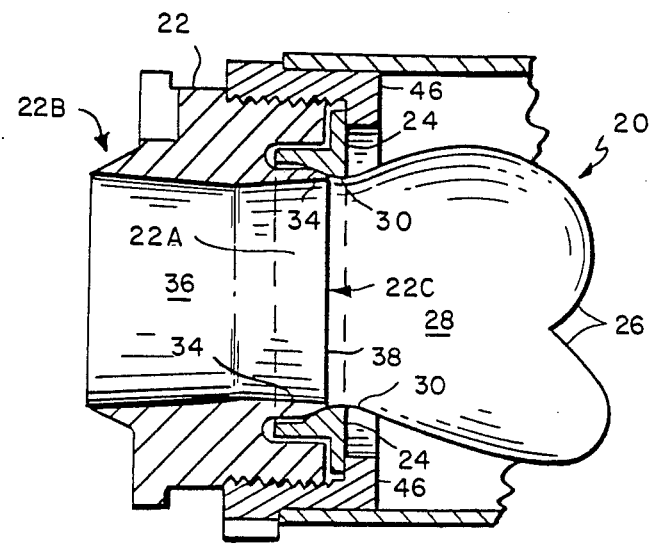
FIG. 3 is a cross-sectional view of a connector of the present invention in combination with an artificial valve.
Figure 3A:
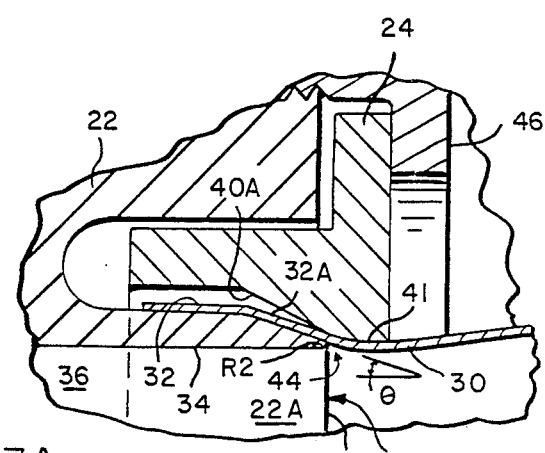
FIG. 3A is an enlarged view of the valve-connector juncture.

The invention illustrated by means of the embodiment described above has general and obvious applicability to other connections within the blood circulatory path of extracorporeal blood handling systems. Wherever a flexible component through which blood flows is connected to another component, the resulting discontinuity at the point where the flexible component meets the connector creates a site at which serious blood clotting problems tend to occur. The invention disclosed herein can be utilized at those junctions to minimize or eliminate the clotting problems. For example, FIGS. 3 and 3A illustrate another connection which embodies the invention. They show a cross-section of a connector which is used to connect a valve assembly into the blood flow path of an extra-corporeal blood handling system. The connector comprises a valve assembly 20, a coupler 22 and a collar 24. Blood which passes through the valve assembly 20 is transmitted to other components in the extracorporeal blood handling system through the coupler 22.

The valve assembly 20, similar to an artificial heart valve, includes a plurality of valve leaflets 26 supported inside a conduit 28 which has a wall 30. The conduit 28 is made of a flexible, polymeric material that is compatible with blood such as a polyurethane elastomer.

Coupler 22, to which the valve assembly 20 is coupled, is generally tubular in shape and is made of a rigid, blood compatible material such as polycarbonate. The coupler 22 has an inside surface 34 defining a bore 36 which extends through the coupler and provides a passage through which blood can flow. At one end of the coupler 22, there is a coupling section 22B which mates with another component in the blood handling system such as a blood pump (not shown in the illustrations). At the other end of the coupler 22, there is a connecting section 22A to which the valve assembly 20 attaches. The connecting section 22A has an outer surface 32 which has a tapered portion 32A that meets the inside surface 34 to form a thin rounded edge 38 at the distal end 22C of conduit 22. Tapered portion 32A tapers inward at taper angle $\phi$ from the axis of bore 36, corresponding to the same taper angle in the previous embodiment. The rounded edge 38 has a radius of curvature R2. At the distal end 22C, just inside edge 38, the bore 36 has a diameter D5. When the flexible conduit 28 is connected to the coupler 22, the wall 30 of conduit 28 fits over and conforms to the tapered portion 32A in the vicinity of distal end 22C.

Figure 4:
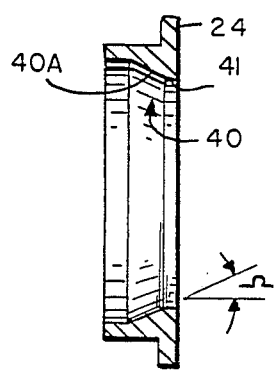
FIG. 4 is a cross-sectional view of the collar of the connector shown in FIG. 3.

As illustrated in FIG. 4, the collar 24 is ring shaped and has an inner surface 40 with a tapered portion 40A, which tapers outward at taper angle $\Omega$ from the bore of the collar, corresponding to the same taper angle in the previous embodiment. In this embodiment, taper angle $\Omega$ is preferably from 5 to 10 degrees greater than taper angle $\phi$. The inner tapered portion 40A of the collar 24 has a length approximately equal to the length of the outer tapered portion 32A of the coupler 22. The tapered portion 40A restricts down to an inside diameter of D6 which is no larger than the sum of the diameter D5 of the bore 36 at the outer end 22C plus twice the thickness of the wall 30. The diameter D6, however, is not so small as to distort the generally circular shape of the conduit 28 when it is passed through the collar 24 as described hereinafter.

Collar 24 also includes a tubular neck section 41 which has an inner diameter through its length equal to or less than the diameter D6 at the narrowest point of tapered portion 40A. Neck section 41 limits the flexing of conduit 28 in the vicinity of the juncture region 44, and thereby minimizes disturbances in the flow of blood through this region.

The components are assembled in a manner similar to the assembly procedure described above for the blood tubing connector. Conduit 28 is inserted through collar 24 so that it is encircled by the collar. Then, conduit 28 is fitted over connecting section 22A of coupler 22 so that it closely conforms to the tapered portion 32A of the outer surface 32 and forms a juncture 44 in the vicinity of edge 38 where conduit 28 meets coupler 22. Next, collar 24 is pushed down over the connection formed by conduit 28 and coupler 22 so that the inner surface 40A compresses the wall 30 against the tapered portion 32A.

To facilitate assembly of conduit 28 over outer tapered portion 32A, taper angle $\phi$ should preferably fall within the range of 15 to 25 degrees. Due to the relative size of the two taper angles $\phi$ and $\Omega$, coupled with the size limitation on the diameter D6, collar 24 focuses the compression of conduit 28 near the outer end 22C of coupler 22. Thus, as with the blood tubing connection described above, the compression of the conduit 28 between the inner tapered portion 40A of the collar 24 and the outer tapered portion 32A of the coupler 22 forms a seal at the juncture 44 in the vicinity of the edge 38.

The seal prevents the conduit 28 from separating from the connecting section 22A, thereby preventing gaps from forming in the vicinity of the edge 38 which would create generation sites for blood clots. In addition, the compression of the conduit 28 in the vicinity of the juncture 44 encourages conduit 28 to conform to the tapered portion 32A around the edge 38 thereby reducing any discontinuity that exists at the juncture 44. If the radius of curvature R2 of the edge 38 is greater than about 0.005 inches but less than about 0.010 inches, the edge 38 will be durable enough to resist deforming under use and, at the same time, small enough to not provoke serious blood clotting problems in the vicinity of the edge 38 when the collar 24 is in place.

A variety of methods, well known to those skilled in the art, can be used to retain the collar 24 in the assembled position. One such method is illustrated in FIG. 3. A retaining ring 46 is threaded onto the valve coupler 22 and holds the collar 24 in place.

Figure 5:
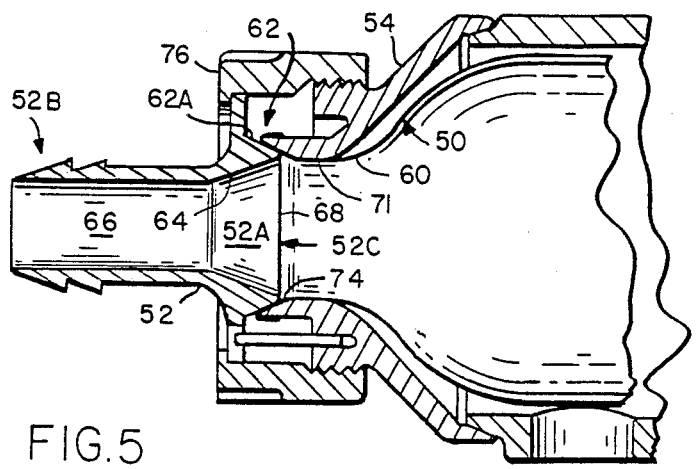
FIG. 5 is a cross-sectional view of a connector of the present invention in combination with a blood-pump bladder.
Figure 5A:
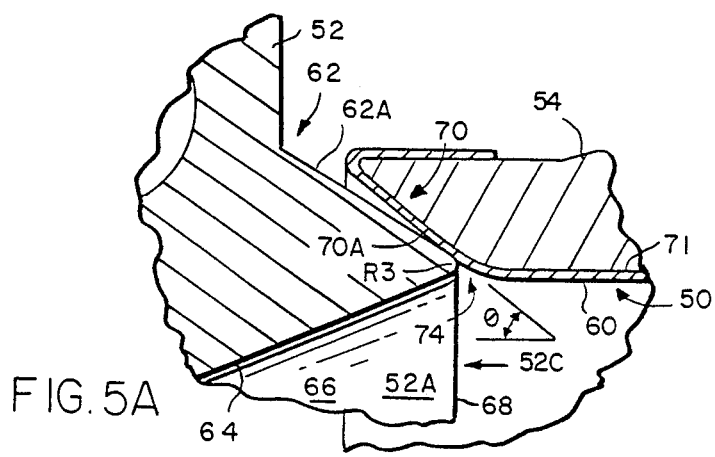
FIG. 5A is an enlarged view of the bladder-connector juncture.

Yet a third embodiment of the invention is illustrated in FIGS. 5 and 5A, which show a cross-section of a bladder connection used on a blood pump. As illustrated, the bladder connection comprises a bladder 50, a bladder coupler 52 and a bladder collar 54.

The bladder 50 is generally tubular in shape with an opening at either end. It has a wall 60 and is made of a flexible, polymeric blood-compatible material such as a polyurethane elastomer. The inside of bladder 50 forms a chamber 50A through which blood passes. By periodically compressing and expanding bladder 50, blood is forced out of and drawn into bladder chamber 50A. When one end of bladder 50 is coupled to a one-way valve, such as the valve 20 illustrated in FIG. 3, the periodic compressions and expansions of the bladder propel the blood in one direction through the blood handling system to which it is attached. The means for compressing and expanding bladder 50 are not illustrated in the figures but such means are well known to persons skilled in the art.

The bladder coupler 52 is generally tubular in shape and is made of a rigid, blood-compatible material such as polycarbonate. The coupler 52 has an inside surface 64 defining a bore 66 which extends through coupler 52 and provides a passage through which blood can flow. At one end of coupler 52, there is a coupling section 52B which mates with another component in the blood handling system such as a blood tubing. At the other end of coupler 52, there is a connecting section 52A which connects to the bladder 50. The connecting section 52A has an outer surface 62 which has a tapered portion 62A that meets the inside surface 64 to form a thin rounded edge 68 at the distal end 52C of the coupler. Tapered portion 62A tapers inward at taper angle $\phi$ from the axis of bore 66, as with the correspondingly identified coupler taper angles in the previous embodiments. Also as in the previous embodiments, taper angle $\phi$ is preferably within the range of 15 to 25 degrees. The rounded edge 68 has a radius of curvature R3. At the distal end 52C, just inside edge 68, the bore 66 has a diameter D7. When bladder 50 is connected to bladder coupler 52, wall 60 of bladder 50 fits over and conforms to tapered portion 62A in the vicinity of the distal end 52C.

Figure 6:
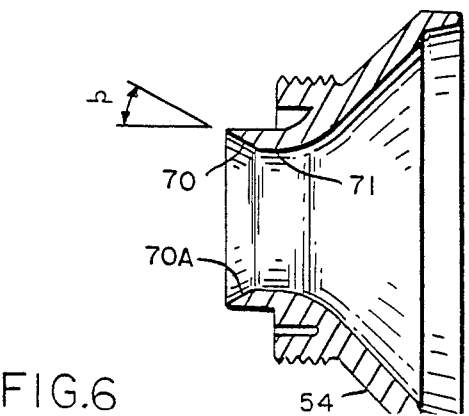
FIG. 6 is a cross-sectional view of the collar of the connector shown in FIG. 5.

The bladder collar 54, which is more clearly illustrated in the cross-sectional view of FIG. 6, is ring shaped and has an inner surface 70 with a taper portion 70A which tapers outward at taper angle $\Omega$ from the axis of the bore of the collar, as with the correspondingly identified collar taper angles in the previous embodiments. In this embodiment, as in the previous valve-connector embodiment, the angle $\Omega$ is preferably from 5 to 10 degrees greater than the angle $\phi$. The tapered portion 70A restricts down to an inside diameter D8 which is no larger than the sum of the diameter D7 of bore 66 at outer end 52C plus twice the thickness of bladder wall 60. The diameter D8, however, is not so small as to adversely distort bladder 50 when it is inserted through the collar 54 as described hereinafter.

Bladder collar 54 also includes a tubular neck section 71 which has an inner diameter through its length equal to or less than the diameter D8 at the narrowest point of tapered portion 70A. As described in relation to the previous embodiment, neck section 71 limits the flexing of bladder 50 in the vicinity of the juncture region 74, and thereby minimizes disturbances in the flow of blood through this region.

In the assembled connection, the bladder collar 54 functions in substantially the same manner as the collars 7 and 24 described in the other embodiments above. The assembly of the bladder connection, however, is slightly different from the previously described procedures since the bladder 50 is typically supported in a blood pump housing prior to connection to other components in the blood handling system. To facilitate assembly, collar 54 is incorporated into the blood pump housing and provides the means for supporting bladder 50 so that it can be connected to coupler 52 when the pump is put in the blood handling system. Thus, the end of bladder 50 which is to be connected to coupler 52 is inserted through bladder collar 54 in the direction of restriction so that bladder 50 extends out the other side of collar 54. The end of bladder 50 is then folded back over collar 54 so that it encircles the outside circumference of the end of collar 54. With the bladder thus fitted into collar 54, wall 60 of bladder 50 conforms to the inner surface 70A of the tapered section 70 and collar 54 supports bladder 50.

To connect the blood pump into the blood handling system, bladder coupler 52 is inserted into bladder collar 54 so that the tapered portion 62A of the coupler outer surface 62 compresses the bladder wall 60 against the inner tapered portion 70A of the collar. When assembled thusly, a juncture 74 is formed in the vicinity of the thin rounded edge 68 where bladder 50 meets coupler 52. As in the other embodiments, the compression of the bladder wall 60 between the inner tapered portion 70A and the outer tapered portion 62A forms a seal in the vicinity of the edge 68. Again, it is preferable that the radius of curvature R3 be greater than about 0.005 inches but less than about 0.010 inches to achieve acceptable durability and at the same time maintain the discontinuities in the assembled connection within acceptable limits. If R is kept substantially around this range, the discontinuity between the bladder wall 60 and the inside surface 64 of the coupler 52 in the assembled connection will not constitute a serious blood clot generation site.

In the embodiment illustrated in FIG. 5, the collar 54 is held in place by a retaining ring 76 which is threaded onto collar 54 and urges coupler 52 into collar 54. The retaining ring 76 assists in maintaining a constant compression of the bladder in the vicinity of juncture 74 and prevents collar 54 from being dislodged from coupler 52. Of course, the retaining ring 76 is merely illustrative of one of many alternatives methods of holding the collar 54 in place.

The connections described herein, which embody the invention, do not exhibit the serious blood clotting problems which are typically associated with connections found in the prior art. The invention substantially reduces the occurrence and magnitude of discontinuities at the point where the flexible component meets the coupler so that the connection does not provide a generation site for blood clots.

If blood handling systems are assembled without the benefit of this invention, the blood clotting problems at component connection locations are typically quite serious. A frequently selected solution to the clotting problem at such points has been to avoid using couplers within the blood handling system wherever possible. A good example, is found within the blood pump itself. Some pumps comprise a combination of bladders and valves hooked in series. Instead of using connectors to couple these components together, the entire assembly is fabricated as one continuous, unitary structure. By providing a smooth continuous inner wall through the structure, the unitary construction avoids the discontinuities caused by using couplers and thus avoids a major cause for blood clotting. However, fabricating unitary construction blood pumps is substantially more difficult and therefore considerably more expensive than using coupled components. With the use of the invention described herein, blood pumps can be produced much less expensively without paying a penalty of significantly greater blood clotting problems.

I claim:

1. A connector for connecting a flexible conduit, which is used to contain blood flow in an extra-corporeal blood handling system, to a second component in said system, said connector comprising:
   A. a generally tubular coupler having
      1. a proximal coupling section for connecting to said second component, and
      2. a distal coupling section for connecting to said flexible conduit, said distal coupling section having an outer tapered portion which tapers inward to an edge having a finite thickness at the distal end of said coupler;
   B. a generally ring-shaped compression collar having an inner tapered portion for encircling the outer tapered portion of said distal coupling section, the angle of taper of said inner tapered portion being at least as large as the angle of taper of said outer tapered portion, and
   C. said compression collar being relatively rigid and incompressible, whereby when said collar is assembled over said distal coupling section with the flexible conduit therebetween, said inner tapered portion compresses the flexible conduit against said outer tapered portion and focuses the compression in the vicinity of said distal end of the coupler.

2. The blood tubing connector of claim 1 wherein said edge of said coupler has a width which has a radius of curvature in the range of about 0.005 to 0.010 inches.

3. The blood tubing connector of claim 1 wherein the angle of taper of said outer tapered portion of said distal coupling section is in the range of about 15 to 25 degrees.

4. The blood tubing connector of claim 37 wherein the angle of taper of said inner tapered portion of said collar is in the range of about 0 to 5 degrees larger than the angle of taper of said outer tapered portion of said distal coupling section.

5. The blood tubing connector of claim 4 wherein said collar further includes a tubular-shaped neck section adjacent the narrower end of said inner tapered portion, said neck section encircling said tubing and extending away from said coupler when said coupler, tubing and collar are assembled, and said neck section having an inside diameter slightly less than the outside diameter of said tubing, whereby said neck section prevents said tubing from flexing in the vicinity said coupler.

6. A blood tubing connector for connecting flexible tubing, which has a uniform inner diameter and which is used to contain blood flow in an extra-corporeal blood handling system, to a second component in said system, said connector comprising:
 A. a generally tubular coupler, with a proximal end and a distal end, said coupler having:
  1. a proximal coupling section for connecting to said second component, and
  2. a distal coupling section for connecting to said flexible tubing, said distal coupling section having:
   a. an outer tapered portion which tapers inward to a thin edge at the distal end of said coupler, said edge being sufficiently thin to avoid formation of blood clots at the juncture of said tubing and said coupler near said edge; and
   b. an inner diameter equal to the inner diameter of said flexible tubing; and
 B. a generally ring-shaped relatively rigid and incompressible compression collar having an inner tapered portion with a fixed angle of taper for encircling the outer tapered portion of said distal coupling section, the angle of taper of said inner tapered portion being at least as large as the angle of taper of said outer tapered portion, and said inner tapered portion tapering down to an inside diameter which is smaller than the outside diameter of said flexible tubing,
whereby when said flexible tubing is stretched over said distal coupling section of the coupler and said collar is then assembled thereover with the flexible tubing between the distal coupling section and the collar, said inner tapered portion of the collar compresses the flexible tubing against said outer tapered portion of the coupler and focuses the compression in the vicinity of said distal end of the coupler.

* * * * *